United States Patent
Wang et al.

(10) Patent No.: US 7,511,177 B2
(45) Date of Patent: *Mar. 31, 2009

(54) FLUOROADAMANTANE DERIVATIVE

(75) Inventors: Shu-zhong Wang, Yokohama (JP); Taiki Hoshino, Yokohama (JP); Kimiaki Kashiwagi, Yokohama (JP); Takashi Okazoe, Yokohama (JP); Eisuke Murotani, Yokohama (JP); Masahiro Ito, Yokohama (JP); Kunio Watanabe, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/020,863

(22) Filed: Jan. 28, 2008

(65) Prior Publication Data

US 2008/0132736 A1    Jun. 5, 2008

Related U.S. Application Data

(60) Division of application No. 11/567,391, filed on Dec. 6, 2006, now Pat. No. 7,402,714, which is a continuation of application No. PCT/JP2005/010979, filed on Jun. 15, 2005.

(30) Foreign Application Priority Data

Jun. 16, 2004    (JP)    ............... 2004-178331

(51) Int. Cl.
    *C07C 35/22*    (2006.01)
(52) U.S. Cl. .................................. 568/818
(58) Field of Classification Search ............ None
    See application file for complete search history.

(56) References Cited

U.S. PATENT DOCUMENTS

| | | | |
|---|---|---|---|
| 4,284,558 | A | 8/1981 | Barton et al. |
| 7,084,295 | B2 * | 8/2006 | Tanaka et al. ............ 560/219 |
| 7,326,512 | B2 | 2/2008 | Ogata et al. |
| 2005/0277785 | A1 | 12/2005 | Okazoe et al. |
| 2005/0288528 | A1 | 12/2005 | Okazoe et al. |
| 2008/0132736 | A1 | 6/2008 | Wang et al. |

FOREIGN PATENT DOCUMENTS

JP    51-4102    1/1976

OTHER PUBLICATIONS

James L. Adcock, et al., "Polarized C-H Groups as Novel Hydrogen-Bond Donors in Hydryl-F-Alkyl Esters: Unequivocal Examples for the Pinchas Effect", J. Org. Chem., 1995, vol. 60, No. 7, pp. 1999 to 2002.

(Continued)

*Primary Examiner*—Daniel M Sullivan
*Assistant Examiner*—Yevegeny Valenrod

(74) *Attorney, Agent, or Firm*—Oblon, Spivak, McClelland, Maier & Neustadt, P.C.

(57) ABSTRACT

Adamantane derivates which can be material compounds of a polymer excellent in etching resistance and having improved transmittance to light having a short wavelength, are produced by an economically advantageous process from readily available materials.

A compound (10) is subjected to esterification reaction with a compound (11) to obtain a compound (12), which is subjected to fluorination in a liquid phase to obtain a compound (13), which is then subjected to hydrolysis or alcoholysis to obtain a compound (2), which is then reacted with a compound (15) thereby to obtain a compound (1). Here, A to J are —CFH— or —CF$_2$—; R$^F$ is a perfluoroalkyl group or the like; X$^{10}$ is F or the like; Y$^2$ is H or OH; Y$^3$ is H or R$^F$COO—; Y$^4$ is H, F or R$^F$COO—; Y$^5$ is H, F, R$^F$COO— or OH; Y$^0$ is H, F, —OCOCR$^1$=CH$_2$ or OH; R$^1$ is a hydrogen atom, a methyl group or the like; and X$^{11}$ is OH or a halogen atom:

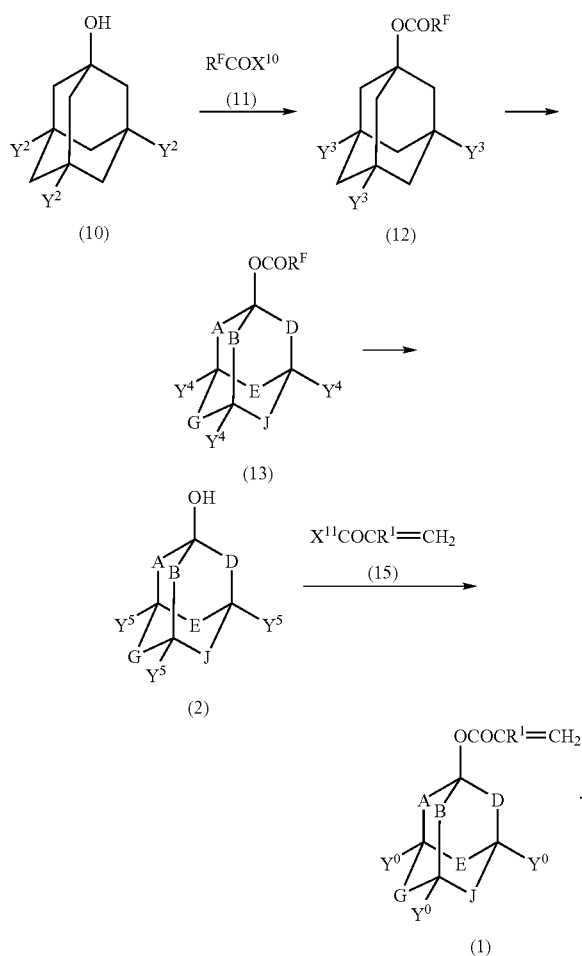

2 Claims, No Drawings

FOREIGN PATENT DOCUMENTS

| | | | |
|---|---|---|---|
| JP | 4-502319 | | 4/1992 |
| JP | 9-43848 A | | 2/1997 |
| JP | 2003-280205 | | 10/2003 |
| JP | 2004-123687 A | | 4/2004 |
| JP | 2005-23066 A | | 1/2005 |
| JP | 20205-89363 A | | 4/2005 |
| WO | WO03/055541 | * | 7/2003 |
| WO | WO 03/055841 | | 7/2003 |
| WO | WO 2004/052832 A1 | | 6/2004 |

OTHER PUBLICATIONS

James L. Adcock, et al., "Highly Fluorinated Adamantanols: Synthesis, Acidities, and Reactivities", J. Org. Chem., 1996, vol. 61, No. 15. pp. 5073 to 5076.

Dan Farcasiu et al., J. Am. Chem. Soc., "Relative Reactivity of BridgeHead Adamantyl and Homoadamantyl Substrates From Solvolyses With Heptafluorubutyrate as a Highly Reactive Carboxylate Leaving Group. Absence of SN2 Character of Solvolysis of tert-Butyl Derivatives", 1985, vol. 107 No. 2, pp. 5717-5722.

Muthiah Manoharan et al., Tetrahedron Letters, "Lipidic Nucleic Acids", 1995, vol. 36, No. 21, pp. 3651-3654.

James L. Adcock et al., J. Org. Chem., "Aerosol Fluorination of 1-Chloroadamantane, 2-Chloroadamantane, and Methyl 1-Adamantylacetata: a Novel Synthetic Approach to 1- and 2-Substituted Hydryl-, Methyl-, and (Difluoromethyl)-f-Adamantanes", 1992, vol. 57, No. 17, pp. 4749-4752.

H. Duddeck, et al., "Synthesen Und $^{13}$C-NMR-Spektroskopische Untersuchungen Trifluormethylsubstituierter Adamantane", Liebigs Ann. Chem, 1985, pp. 545-554.

U.S. Appl. No. 12/091,846, filed Apr. 28, 2008, Wang, et al.

* cited by examiner

FLUOROADAMANTANE DERIVATIVE

CROSS REFERENCE TO RELATED APPLICATIONS

This application is a divisional application of prior U.S. patent application Ser. No. 11/567,391, filed Dec. 6, 2006, now U.S. Pat. No. 7,402,714, issued Jul. 22, 2008. The parent is a continuation application of PCT/JP05/10979, filed Jun. 15, 2005.

TECHNICAL FIELD

The present invention relates to a novel fluoroadamantane derivative. More particularly, the present invention relates to a fluoroadamantane compound having from one to four hydroxyl groups bonded to a tertiary carbon atom in the fluoroadamantane skeleton (hereinafter referred to as hydroxyfluoroadamantane) and a compound having a hydroxyl group of such hydroxyfluoroadamantane converted by an acrylic acid derivative. Further, it provides a process for producing such a compound employing liquid phase fluorination, and a novel intermediate for the production process.

BACKGROUND ART

Non fluorine type adamantane derivatives are useful, in etching in which photolithography is applied, as e.g. a compound constituting an etching resistant thin membrane material to protect the substrate layer.

As fluorinated adamantane derivates, (perfluoroadamanty-l)acrylates and diacrylates are disclosed in a document (see Patent Document 1).

Further, a process for producing 1-hydroxyperfluoroadamantane, 2-hydro-1-hydroxyperfluoroadamantane and 2-hydro-1,3-dihydroxyperfluoroadamantane by aerosol fluorination has been reported (see Non Patent Documents 1 to 3).

Patent Document 1: WO03/55841
Non Patent Document 1: Adocock, James L. et al., Journal of Organic Chemistry, 1995, Vol. 60, p. 1999-2002.
Non Patent Document 2: Adocock, James L. et al., Journal of Organic Chemistry, 1996, Vol. 61, p. 5073-5076.
Non Patent Document 3: Adocock, James L. et al., Journal of Organic Chemistry, 1992, Vol. 57, p. 4297-4300.

DISCLOSURE OF THE INVENTION

Problems that the Invention is to Solve

Patent Document 1 discloses a chemical formula of acrylate of perfluoroadamantane but there are no grounds for a method to obtain such a compound or availability of such a compound. For example, 1-hydroxyperfluoroadamantane as a production material is hardly available, and its preparation process and preparation examples are not disclosed at all. Further, the present inventors have produced 1-hydroxyperfluoroadamantane, but no compound showing the spectrum data disclosed in Patent Document 1 has been obtained.

Non Patent Documents 1 to 3 disclose a fluorination method by aerosol fluorination. This fluorination method is a means of bringing fluorine gas into contact with the surface of a solid substrate, and accordingly, the reaction will take place only at the surface of the substrate, whereby it is very difficult to achieve a high yield by this method. Particularly, fluorination of 1,3,5-trihydroxy form or 1,3,5,7-tetrahydroxy form of perfluoroadamantane by the above method is expected to be very difficult, and this method cannot be employed as an industrial production process. Further, with respect to the trihydroxy form and the tetrahydroxy form, no practical preparation example has been disclosed.

Means to Solve the Problems

The present inventors have conceived that a fluorinated adamantane derivative may be a material which is more excellent in transparency to light having a short wavelength, which is more excellent in etching resistance and which can be applied to microphotolithography, optical adhesives, etc. Thus, they have found that a hydroxyfluoroadamantane which may be a material of such a derivative can be produced by an industrially applicable process. More particularly, they have realized a process for producing a compound having a fluorinated adamantane skeleton and having one to four hydroxyl groups bonded to a tertiary carbon atom at the 1-, 3-, 5- or 7-position in the adamantane group, by a novel producing route employing liquid phase fluorination from an available compound having an adamantane skeleton. They have further realized a process for producing a novel compound having both one fluorinated adamantane skeleton and one to four acrylic acid derivate groups, by reacting such a compound with an acrylic acid derivate.

Namely, the present invention provides the following.

1. A process for producing a compound represented by the following formula (1), which comprises subjecting a compound represented by the following formula (10) to esterification reaction with a compound represented by the following formula (11) to obtain a compound represented by the following formula (12), subjecting the compound represented by the formula (12) to fluorination in a liquid phase to obtain a compound represented by the following formula (13), subjecting the compound represented by the formula (13) to hydrolysis or alcoholysis to obtain a compound represented by the following formula (2), and reacting the compound represented by the formula (2) with a compound represented by the following formula (15):

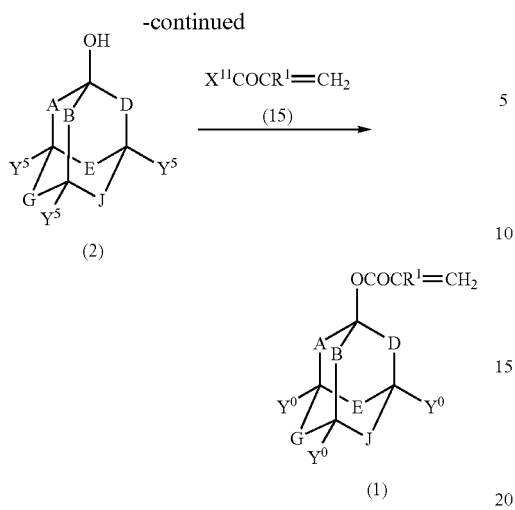

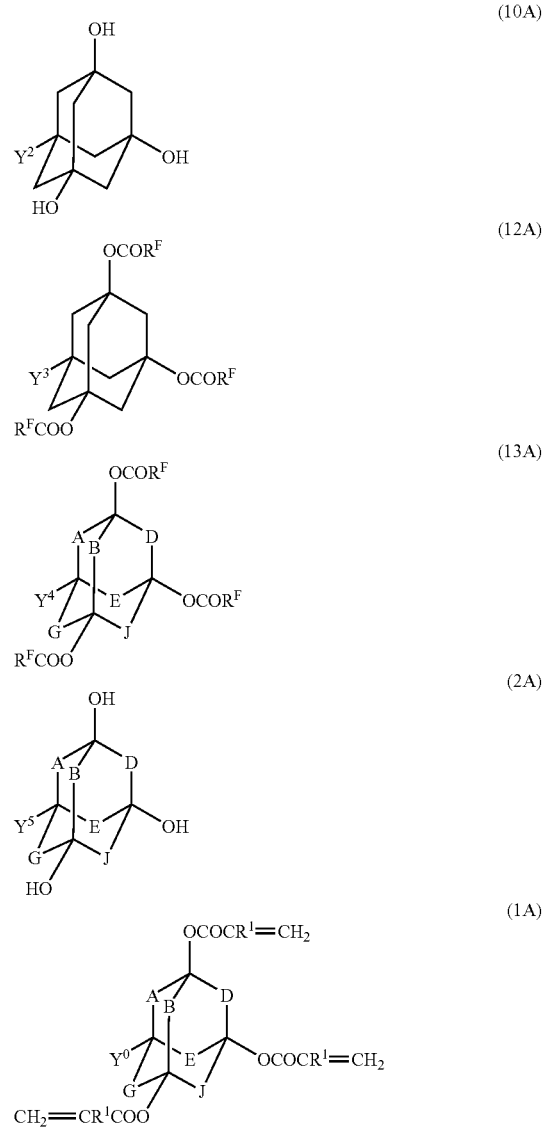

provided that the symbols in the formulae have the following meanings:

A, B, D, E, G, J: each of them which may be the same or different, is —CFH— or —CF$_2$—;

R$^F$: a perfluorinated monovalent saturated organic group;

X$^{10}$: a halogen atom;

R$^1$: a hydrogen atom, a methyl group, a fluorine atom or a trifluoromethyl group;

X$^{11}$: a hydroxyl group or a halogen atom;

Y$^2$: each of three Y$^2$s which may be the same or different, is a hydrogen atom or a hydroxyl group;

Y$^3$: Y$^3$ corresponding to Y$^2$ which is a hydrogen atom, is a hydrogen atom, and Y$^3$ corresponding to Y$^2$ which is a hydroxyl group, is a group represented by R$^F$COO— (wherein R$^F$ is as defined above);

Y$^4$: Y$^4$ corresponding to Y$^3$ which is a hydrogen atom, is a hydrogen atom or a fluorine atom, and Y$^4$ corresponding to Y$^3$ which is a group represented by R$^F$COO—, is a group represented by R$^F$COO— (wherein R$^F$ is as defined above);

Y$^5$: Y$^5$ corresponding to Y$^4$ which is a hydrogen atom, is a hydrogen atom, Y$^5$ corresponding to Y$^4$ which is a fluorine atom, is a fluorine atom, and Y$^5$ corresponding to Y$^4$ which is a group represented by R$^F$COO—, is a hydroxyl group (wherein R$^F$ is as defined above); and Y$^0$: Y$^0$ corresponding to Y$^5$ which is a hydrogen atom, is a hydrogen atom, Y$^0$ corresponding to Y$^5$ which is a fluorine atom, is a fluorine atom, and Y$^0$ corresponding to Y$^5$ which is a hydroxyl group, is a group represented by —OCOCR$^1$=CH$_2$ (wherein R$^1$ is as defined above) or a hydroxyl group.

2. The production process according to 1, wherein the compound represented by the formula (10) is a compound represented by the following formula (10A), the compound represented by the formula (12) is a compound represented by the following formula (12A), the compound represented by the formula (13) is a compound represented by the following formula (13A), the compound represented by the formula (2) is a compound represented by the following formula (2A), and the compound represented by the formula (1) is a compound represented by the following formula (1A):

provided that the symbols in the formulae are as defined above.

3. A compound represented by the following formula (1'):

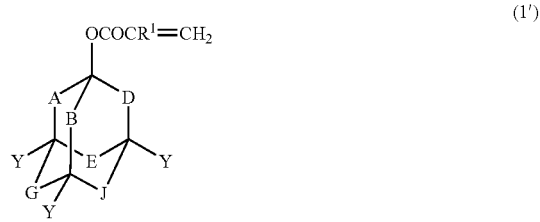

provided that the symbols in the formula have the following meanings:

A, B, D, E, G, J: each of them which may be the same or different, is —CFH— or —CF$_2$—;

$R^1$: a hydrogen atom, a methyl group, a fluorine atom or a trifluoromethyl group; and Y: a group represented by the formula —OCO—$CR^{10}$=$CH_2$ (wherein $R^{10}$ is a hydrogen atom, a methyl group, a fluorine atom or a trifluoromethyl group), a hydrogen atom, a fluorine atom or a hydroxyl group, provided that three Ys may be the same or different.

4. The compound according to 3, wherein in the formula (1'), A, B, E, G and J are —$CF_2$—, D is —CFH—, and Y is a group represented by the formula —OCO—$CR^{10}$=$CH_2$, a fluorine atom or a hydroxyl group, provided that three Ys may be the same or different.

5. A compound represented by the following formula (1A')

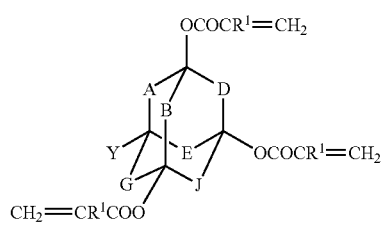

(1A')

provided that the symbols in the formula have the following meanings:

A, B, D, E, G, J: each of them which may be the same or different, is —CFH— or —$CF_2$—;

$R^1$: a hydrogen atom, a methyl group, a fluorine atom or a trifluoromethyl group; and Y: a hydrogen atom, a fluorine atom, a hydroxyl group or a group represented by the formula —OCO—$CR^{10}$=$CH_2$ (wherein $R^{10}$ is a hydrogen atom, a methyl group, a fluorine atom or a trifluoromethyl group).

6. The compound according to 5, wherein in the formula (1A'), A, B, D, E, G and J are —$CF_2$—, and Y is a group represented by the formula —OCO—$CR^{10}$=$CH_2$, a fluorine atom or a hydroxyl group.

7. The compound according to 5, wherein in the formula (1A'), A, B, E, G and J are —$CF_2$—, D is —CFH—, and Y is a group represented by the formula —OCO—$CR^{10}$=$CH_2$, a fluorine atom or a hydroxyl group.

8. A compound represented by the following formula (1B):

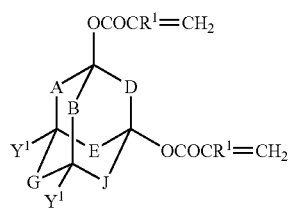

(1B)

provided that the symbols in the formula have the following meanings:

A, B, D, E, G, J: each of them which may be the same or different, is —CFH— or —$CF_2$—;

$Y^1$: a hydrogen atom, a fluorine atom or a hydroxyl group, provided that two $Y^1$s may be the same or different; and $R^1$: a hydrogen atom, a methyl group, a fluorine atom or a trifluoromethyl group.

9. The compound according to 8, wherein in the formula (1B), A, B, E, G and J are —$CF_2$—, D is —CFH—, and $Y^1$ is a hydroxyl group or a fluorine atom.

10. A compound represented by the following formula (1C):

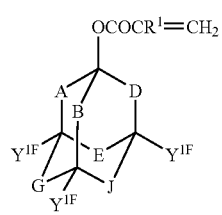

(1C)

provided that the symbols in the formula have the following meanings:

A, B, D, E, G, J: each of them which may be the same or different, is —CFH— or —$CF_2$—;

$Y^{1F}$: a fluorine atom or a hydroxyl group, provided that three $Y^{1F}$s may be the same or different; and $R^1$: a hydrogen atom, a methyl group, a fluorine atom or a trifluoromethyl group.

11. A compound represented by the following formula (1CF-1), wherein in $^1$HNMR spectrum (solvent: $CDCl_3$, standard substance: tetramethylsilane), the chemical shifts (unit: ppm) are 6.08, 6.25 and 6.57, and in $^{19}$FNMR spectrum (solvent $CDCl_3$, standard substance: $CFCl_3$), the chemical shifts (unit: ppm) are −114.7, −121.2 and −221.6:

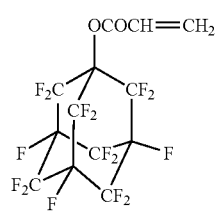

(1CF-1)

12. A compound represented by the following formula (1CH):

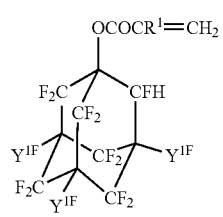

(1CH)

provided that the symbols in the formula have the following meanings:

$Y^{1F}$: a fluorine atom or a hydroxyl group, provided that three $Y^{1F}$s may be the same or different; and $R^1$: a hydrogen atom, a methyl group, a fluorine atom or a trifluoromethyl group.

13. A compound represented by the following formula (1CH-1), wherein in $^1$HNMR spectrum (solvent: $CDCl_3$, standard substance: tetramethylsilane), the chemical shifts (unit: ppm) are 6.16, 6.24, 6.64 and 6.77, and in $^{19}$FNMR spectrum (solvent CDCl$_3$, standard substance: CFCl$_3$), the chemical shifts (unit: ppm) are −113.4 to −124.8, −212.5, −222.2 and −222.9:

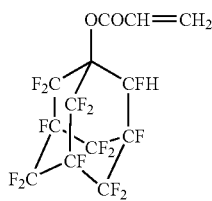

(1CH-1)

14. A compound represented by the following formula (2A'):

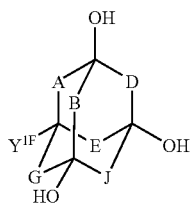

(2A')

provided that the symbols in the formula have the following meanings:

$Y^{1F}$: a fluorine atom or a hydroxyl group; and

A, B, D, E, G, J: each of them which may be the same or different, is —CFH— or —CF$_2$—.

15. The compound according to 14, wherein A, B, E, G and J are —CF$_2$—, and D is —CFH—.

16. A compound represented by the following formula (2AF):

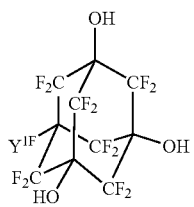

(2AF)

provided that $Y^{1F}$ is a fluorine atom or a hydroxyl group.

17. A compound represented by the following formula (2BF):

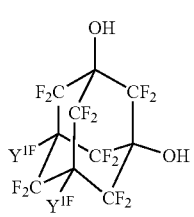

(2BF)

provided that each $Y^{1F}$ is a fluorine atom or a hydroxyl group.

18. The compound according to 17, wherein $Y^{1F}$ is a fluorine atom, and in $^{19}$FNMR (solvent CD$_3$OD, standard substance: CFCl$_3$) spectrum, the chemical shifts (unit: ppm) are −117.6 to −124.4 and −221.5 to −224.5.

19. A compound represented by the following formula (13):

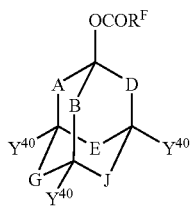

(13)

provided that the symbols in the formula have the following meanings:

A, B, D, E, G, J: each of them which may be the same or different, is —CFH— or —CF$_2$—;

$R^F$: a perfluorinated monovalent saturated organic group;

$Y^{40}$: a hydrogen atom, a fluorine atom or a group represented by $R^F$COO—, and three $Y^{40}$s may be the same or different.

20. The compound according to 19, wherein A, B, D, E, G and J are —CF$_2$—, and $Y^{40}$ is a fluorine atom or a group represented by $R^F$COO—, provided that three $Y^{40}$s may be the same or different.

Effects of the Invention

According to the production process of the present invention, an adamantane derivative which may be a material compound of a polymer having excellent etching resistance and improved transparency to light having a short wavelength, can be produced by an economically advantageous process from a readily available material. A polymer produced by the process of the present invention can be suitably used as e.g. a material for microprocessing technology having excellent etching resistance and improved transparency to light having a short wavelength.

BEST MODE FOR CARRYING OUT THE INVENTION

In this specification, a compound represented by the formula (1) will be referred to as the compound (1). The same applies to compounds represented by other formulae.

The compound (1) of the present invention can be produced by a process which comprises subjecting a compound (10) to esterification reaction with a compound (11) to obtain a compound (12), subjecting the compound (12) to fluorination in a liquid phase to obtain a compound (13), subjecting the compound (13) to hydrolysis or alcoholysis to obtain a compound (13), and reacting the compound (13) with a compound (15) to obtain the compound (1). Preferred embodiments regarding the symbols in these compounds will be described below.

The compound (10) is a known compound disclosed in e.g. JP-A-63-307844. $Y^2$ in the compound (10) is a hydrogen atom or a hydroxyl group, and three $Y^2$s may be the same or different.

The compound (11) is a compound which can be produced by a known method. For example, the compound (11) wherein $X^{10}$ is a fluorine atom can be produced by oligomerization reaction of hexafluoropropylene, a process disclosed in WO00/56694 by the present applicant, or the like. Further, the compound (15) is a compound which is easily available as a commercial product.

$R^F$ in the formula (11) is preferably a perfluoroalkyl group, a perfluoro (partially chlorinated alkyl) group or a perfluoroalkyl group containing an etheric oxygen atom, particularly preferably a perfluoroalkyl group or a perfluoroalkyl group containing an etheric oxygen atom, especially preferably a perfluoroalkyl group, furthermore preferably such a group having from 2 to 20 carbon atoms. The number of carbon atoms of $R^F$ is preferably such that the molecular weight of the compound (12) will be within preferred molecular weight range. Usually, the number of carbon atoms of $R^F$ is preferably from 2 to 20, particularly preferably from 2 to 10.

Among $R^F$, examples of a perfluoroalkyl group include —$CF_2CF_3$, —$CF_2CF_2CF_3$, —$CF_2CF_2CF_2CF_3$, —$CF(CF_3)_2$, —$CF_2CF(CF_3)_2$, —$CF(CF_3)CF_2CF_3$ and —$C(CF_3)_3$. Examples of a perfluoro (partially chlorinated alkyl) group include —$CF_2CClF_2$ and —$CF_2CFClCF_2Cl$. Specific examples of a perfluoroalkyl group containing an etheric oxygen atom include —$CF(CF_3)[OCF_2CF(CF_3)_b]OCF_2CF_2CF_3$ (wherein b is 0 or an integer of at least 1, preferably 0 or an integer of from 1 to 5) and —$(CF_2)_dOCF_3$ (wherein d is an integer of at least 1, preferably an integer of from 1 to 8.

The esterification reaction of the compound (10) with the compound (11) can be carried out under the conditions of known esterification reactions. The lower limit of the reaction temperature for the esterification reaction is preferably $-50°$ C., and the upper limit is preferably $+100°$ C. The reaction time may optionally be changed depending upon the supply rates of the materials and the amount of the compound. The reaction pressure is preferably from atmospheric pressure to 2 MPa (gauge pressure, hereinafter, the pressure is represented by a gauge pressure).

$Y^3$ in the compound (12) corresponds to $Y^2$. $Y^3$ corresponding to $Y^2$ which is a hydrogen atom is a hydrogen atom. $Y^3$ corresponding to $Y^2$ which is a hydroxyl group is a group represented by $R^FCOO$— (wherein $R^F$ is as defined above). Namely, the compound (12) is a compound having all hydroxyl groups in the compound (11) esterified, and is a mono- to tetraester compound.

In the esterification reaction, the amount of the compound (11) to the compound (10) is preferably at least 1 mol. Specifically, the amount of the compound (11) is preferably from 1 to 2 times by mol, particularly preferably from 1 to 1.1 times by mol, relative to the number of mols of hydroxyl groups in the compound (10). When the reaction is carried out in such an amount, it is possible to prevent an unreacted hydroxyl group-containing compound from remaining in the reaction product of the esterification reaction, and it is possible to avoid a side reaction in the fluorination in the subsequent step. Further, the process for purifying the compound (12) can be simplified.

The product of the esterification reaction is preferably purified from such a viewpoint that the fluorination reaction in the subsequent step is smoothly carried out. Especially when the product of the esterification reaction contains a hydroxyl group-containing compound, it is preferred that such a compound is preliminarily removed by purification. The purification method may, for example, be a distillation method, a method wherein the product is treated with e.g. water, followed by liquid separation, a method wherein extraction is carried out with a suitable organic solvent, followed by distillation, silica gel column chromatography, or recrystallization.

In the esterification reaction, hydrofluoric acid (HF) will be formed, and an alkali metal fluoride (NaF or KF is, for example, preferred) or a trialkylamine may be present as a HF capturing agent in the reaction system. The amount of the HF capturing agent is preferably from 0.1 to 10 times by mol relative to the theoretical amount of generated HF. In a case where no HF capturing agent is used, it is preferred that the reaction is carried out at a reaction temperature where HF can be evaporated, so that HF is discharged out of the reaction system as accompanied with a nitrogen stream. Further, a method may be employed wherein the reaction is carried out without using a HF capturing agent, HF is discharged out of the reaction system as accompanied with a nitrogen stream. This method is preferred from such a viewpoint that the crude liquid may be employed as it is in the next fluorination step.

In order to let the liquid phase fluorination reaction in the subsequent step proceed smoothly, the fluorine content of the compound (12) is adjusted to be preferably from 20 to 60 mass %, particularly preferably from 25 to 55 mass %. Further, the molecular weight of the compound (12) is preferably within a range of from 200 to 1,100, particularly preferably within a range of from 300 to 800. With the compound (12) having the fluorine content within the above specified range, the solubility in the liquid phase at the time of the fluorination reaction will be remarkably improved, whereby there will be a merit such that the operation efficiency of the liquid phase fluorination reaction and the reaction yield will be improved and the economical efficiency will be excellent.

The compound (12) can then be converted into the compound (13) by fluorination in a liquid phase. The liquid phase fluorination method of reaction with fluorine ($F_2$) in a liquid phase can remarkably improve the yield of the fluorination reaction and can be employed as an industrial production process to carry out the process of the present invention.

The liquid phase fluorination reaction is carried out by dissolving the compound (12) in a solvent and then reacting it with fluorine in the solvent. The solvent is preferably a solvent inert to the fluorination reaction. Further, the solvent is preferably a solvent in which the solubility of the compound (12) is high, particularly preferably a solvent which is capable of dissolving at least 1 mass %, particularly preferably at least 5 mass %, of the compound (12).

The solvent to be used for the fluorination reaction may, for example, be a known solvent used as a solvent for the liquid phase fluorination. It may, for example, be a chlorofluorocarbon such as R-113 or $CF_2ClCFCl_2$, perfluorotributylamine, a fluorocarbon such as perfluoro(2-butyltetrahydrofuran) or a perfluorinated acyl fluoride. The solvent is preferably a chlorofluorocarbon such as R-113, or a perfluorinated acyl fluoride such as the compound (11). The amount of the solvent is preferably at least 5 times by mass, particularly preferably from $1 \times 10^1$ to $1 \times 10^5$ times by mass, relative to the total mass of the compound (12).

As fluorine, it is preferred to employ fluorine gas itself or fluorine gas diluted with an inert gas. The inert gas is preferably nitrogen gas or helium gas, and nitrogen gas is particularly preferred from the economical reason. The amount of fluorine gas in the nitrogen gas is not particularly limited, but from the viewpoint of the efficiency, it is preferably at least 10 vol %, particularly preferably at least 20 vol %.

Fluorine to be used for the fluorination reaction is preferably maintained so that the amount of fluorine ($F_2$) to the amount of hydrogen atoms contained in the compound (12) will be always in excess by equivalent from the beginning to the end of the reaction. It is preferred from the viewpoint of the selectivity to maintain the amount of fluorine to hydrogen atoms in the compound (12) to be at least 1.05 times by equivalent (i.e. at least 1.05 times by mol), and it is further preferred from the viewpoint of the selectivity to maintain it to be at least twice by equivalent (i.e. at least twice by mol). Further, in order to let the amount of fluorine be in excess by equivalent also at the initiation of the reaction, it is preferred to let fluorine preliminarily be dissolved in a sufficient amount in the solvent for the fluorination reaction to be used at the beginning of the reaction.

It is necessary to carry out the liquid phase fluorination reaction without breaking the ester bond in the compound (12). Accordingly, the reaction temperature is preferably from −50° C. to +100° C., particularly preferably from −20° C. to +50° C. The reaction pressure for the fluorination reaction is not particularly limited, and it is particularly preferred to adjust the pressure to be from atmospheric pressure to 2 MPa from the viewpoint of the reaction yield, the selectivity and the industrial operation efficiency.

In order to let the fluorination reaction proceed efficiently, it is preferred to add a C—H bond-containing compound such as benzene or toluene to the reaction system, to let the compound (12) stay for a long time in a reaction system or to carry out ultraviolet irradiation. Particularly when it is desired to fluorinate all hydrogen atoms in the compound (12), such an operation is preferably carried out. Further, such an operation is carried out preferably at a latter stage of the fluorination reaction.

The fluorination reaction of the present invention is a reaction wherein at least one of hydrogen atoms bonded to a carbon atom in the compound (12) is substituted by a fluorine atom, and preferably, at least 50%, particularly preferably at least 90%, especially preferably at least 95%, of the number of hydrogen atoms, is substituted.

In the liquid phase fluorination, HF is formed as a by-product. For the purpose of removing HF, it is preferred to use a HF capturing agent (preferably NaF), to cool the outlet gas thereby to recover HF, or to discharge HF out of the reaction system as accompanied with an inert gas such as nitrogen gas.

The reaction product of the fluorination reaction may be used as it is in the subsequent step or may be purified to a high purity product. As a purification method, a method of distilling a crude product under atmospheric pressure or under reduced pressure may, for example, be mentioned.

The compound (13) to be formed by the liquid phase fluorination reaction is preferably a compound having the compound (12) perfluorinated (i.e. the compound (13) wherein all of A, B, D, E, G and J are —$CF_2$) or a compound wherein one of hydrogen atoms bonded to carbon atoms adjacent to the carbon atom to which —$OCOR^F$ is bonded of the compound (13) remained non-fluorinated, and all the remaining hydrogen atoms are fluorinated (i.e. D is —CFH—). The reason why the latter compound is formed is considered that in the compound (12), the carbonyl oxygen atom of the —$OCOR^F$ group and the hydrogen atom form a hydrogen bond, whereby the hydrogen atom is less likely to be fluorinated.

In the following, a hydrogen atom bonded to a carbon atom adjacent to the carbon atom to which —$OCOR^F$ is bonded, will be referred to as a "specific hydrogen atom". Further, compounds having all hydrogen atoms other than the specific hydrogen atom in the adamantane skeleton fluorinated will sometimes be generically referred to as a "compound wherein hydrogen remains".

$Y^4$ in the compound (13) corresponds to $Y^3$. $Y^4$ corresponding to $Y^3$ which is a hydrogen atom is a hydrogen atom or a fluorine atom (preferably a fluorine atom). $Y^4$ corresponding to $Y^3$ which is a group represented by $R^FCOO$— (wherein $R^F$ is as defined above) is a group represented by the same $R^FCOO$— as $Y^3$.

The compound (13) is a novel compound provided by the novel production process of the present invention. The compound (13) is useful as an intermediate for production of the compound (1) and the compound (2) as described hereinafter.

Then, in the present invention, the compound (13) is subjected to alcoholysis or hydrolysis to obtain the compound (2). Alcoholysis is decomposition reaction of the compound (13) carried out in the presence of an alcohol, and is carried out preferably in the presence of a compound represented by the formula $R^H$—OH (wherein $R^H$ is a monovalent hydrocarbon group). Further, hydrolysis is a reaction to decompose the compound (13) in the presence of water. Either reaction is carried out usually by heating. Further, the reaction may be carried out under any of elevated pressure, reduced pressure and atmospheric pressure.

$R^H$ may be an alkyl group, a cycloalkyl group or a group wherein one hydrogen atom in adamantane becomes a bond, and such a group preferably has from 1 to 10 carbon atoms. In a case where the compound represented by $R^H$—OH is an alcohol, particularly preferably is a primary or secondary alcohol or a cycloalkanol. Specific examples of the primary alcohol include methanol, ethanol, 2-ethylhexyl alcohol and octanol, specific examples of the secondary alcohol include 2-propanol, 2-buthanol and cyclohexanol, and preferred is a $C_{6-10}$ alcohol. Further, the compound represented by the formula $R^H$—OH is particularly preferably selected from alcohols having a boiling point higher than that of the compound (1) as the aimed product.

Alcoholysis or hydrolysis is carried out preferably under acidic or basic conditions. The acid is preferably hydrochloric acid, sulfuric acid or the like. The base is preferably hydroxide of an alkali metal or hydroxide of an alkaline earth metal. The hydroxide of an alkali metal is preferably NaOH, KOH or CsOH, and NaOH is particularly preferred from economical viewpoint. The decomposition reaction temperature is preferably from 50 to 300° C., particularly preferably from 100 to 250° C. The reaction pressure is not limited.

Alcoholysis or hydrolysis may be carried out in the presence of a reaction solvent. The amount of the reaction solvent is preferably from 0.1 to 10 times relative to the compound (10). Further, in a case where the compound represented by $R^H$—OH is used in excess, this compound may function also as a solvent.

Among the compounds (2) to be formed by the decomposition reaction of the compound (13), compounds wherein the number of hydroxyl groups is at least 2 are compounds of which formation is practically confirmed by the production process of the present invention for the first time. Examples of the compound (2) will be described hereinafter.

The compound (2) is a useful compound capable of being introduced into various useful compounds by conversion of hydroxyl groups. In the present invention, this compound (2) is reacted with the following compound (15) to obtain the compound (1). In the formula, $X^{11}$ is preferably a hydroxyl group, a chlorine atom or a fluorine atom, particularly preferably a fluorine atom. $R^1$ is a hydrogen atom, a methyl group, a fluorine atom or trifluoromethyl group (hereinafter sometimes referred to as $R^{10}$).

$$CH_2{=}CR^1COX^{11} \tag{15}$$

The following compounds may be mentioned as specific examples of the compound (15):

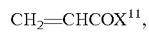

$CH_2{=}CHCOX^{11}$,

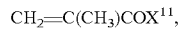

$CH_2{=}C(CH_3)COX^{11}$,

The reaction of the compound (2) with the compound (15) may be carried out by any one of the following methods 1 to 4.

Method 1: The method of subjecting the compound (2) and the compound (15) to azeotropic dehydration under reflux of a solvent.

Method 2: A method of subjecting the compound (2) and the compound (15) to dehydration esterification in the presence of a solvent.

Method 3: A method of subjecting the compound (2) and the compound (15) to esterification reaction in the present of a base.

Method 4: A method of converting the hydroxyl group in the compound (2) into an alkoxide, and then reacting such a compound (2) with the compound (15) wherein Z is a chlorine atom (hereinafter referred to as compound (15Cl)).

In the method 1, the solvent is preferably toluene, xylene or the like. As the reaction conditions for azeotropic dehydration, usual reaction conditions may be employed. The reaction temperature is preferably adjusted to be from −78° C. to 200° C. The reaction pressure is preferably from 0.1 to 10 MPa, and the reaction time is preferably from 1 to 24 hours, particularly preferably from 3 to 6 hours. The amount of the solvent is preferably at least such an amount that the compound (2) has a saturated concentration, particularly preferably such an amount that the concentration of the compound (2) is from 0.5 to 1.0 mol/liter.

In the method 2, the dehydrating agent is preferably molecular sheaves, or an acidic dehydrating agent such as anhydrous sodium sulfate, anhydrous magnesium sulfate or phosphoric anhydride. The solvent may, for example, be an ether solvent such as diethyl ether, tetrahydrofuran or dioxane; an aliphatic hydrocarbon solvent such as hexane, heptane or octane; or an aromatic hydrocarbon solvent such as benzene, toluene or xylene. The reaction temperature in the dehydration esterification reaction is preferably from 25° C. to (the boiling point of the solvent under the reaction pressure), particularly preferably from −78 to +200° C. The reaction pressure is preferably from 0.1 to 10 MPa, particularly preferably atmospheric pressure. The reaction time is preferably from 1 to 24 hours, particularly preferably from 3 to 6 hours. The amount of the solvent used is preferably at least such an mount that the saturation solubility of the compound (2) achieved, and usually particularly preferably such an mount that the concentration of the compound (2) is from 0.5 to 1.0 mol/liter.

In the method 3, the base may, for example, be trimethylamine, triethylamine, pyridine, or N,N-dimethylaniline. The reaction may be carried out with or without a solvent. In a case where a solvent is used, the solvent may, for example, be a halogenated hydrocarbon such as dichloromethane, chloroform, carbon tetrachloride or 1,2-dichloroethane, an ether solvent such as diethyl ether, tetrahydrofuran or dioxane; an aliphatic hydrocarbon solvent such as hexane, heptane or octane; or an aromatic hydrocarbon solvent such as benzene, toluene or xylene. The amount of the solvent is preferably such an amount that the concentration of the compound (2) is from 0.5 to 1.0 mol/liter. The reaction temperature is preferably from −78° C. to +100° C., particularly preferably from −78° C. to +25° C. The reaction pressure is preferably from 0.1 to 10 MPa. The reaction time is preferably from 1 to 24 hours, particularly preferably from 1 to 3 hours.

In the method 4, the method of converting the hydroxyl group of the compound (2) into an alkoxide is preferably carried out by a method of reacting the compound (2) with an alkoxylation agent. The alkoxylation agent may, for example, be lithium metal, sodium metal, potassium metal, n-butyllithium, sec-butyllithium, tert-butyllithium, sodium hydroxide, sodium hydride, sodium borohydride or lithium aluminum hydride. A reaction solvent is preferably used for the reaction. The reaction solvent may, for example, be an ether solvent such as diethyl ether, tetrahydrofuran or dioxane; an aliphatic hydrocarbon solvent such as hexane, heptane or octane; or an aromatic hydrocarbon solvent such as benzene, toluene or xylene.

In the method 4, for the reaction of the alkoxide of the compound (2) with the compound (15), a solvent may or may not be used, but is preferably used. In a case where a reaction solvent is used, it is preferred to use the same solvent as the solvent used for the reaction with the alkoxylation agent. The amount of the reaction solvent is preferably such an amount that the concentration of the compound (15) is from 0.5 to 1.0 mol/liter. The reaction temperature is preferably from −78 to 100° C., particularly preferably from −78° C. to 25° C. The reaction pressure is preferably from 0.1 to 10 MPa. The reaction time is preferably from 1 to 24 hours, particularly preferably from 1 to 3 hours.

In the method 4, the compound (15Cl) can be obtained by reacting the compound (15) with a chlorinating agent. The chlorinating agent is preferably, for example, thionyl chloride, phosphorus pentachloride, phosphorus trichloride, benzoyl chloride or phthaloyl chloride. The reaction with the chlorinating agent may be carried out with or without a solvent. In a case where a solvent is used, the solvent may, for example, be a halogenated hydrocarbon such as dichloromethane, chloroform, carbon tetrachloride or 1,2-dichloroethane; an aliphatic hydrocarbon solvent such as hexane, heptane or octane; or an aromatic hydrocarbon solvent such as benzene, toluene or xylene. The amount of the solvent is preferably such an amount that the concentration of the compound (15) is from 0.5 to 1.0 mol/liter.

The reaction of the compound (15) with the chlorinating agent may be carried out in the presence of a catalyst. The catalyst may, for example, be N,N-dimethylformamide, hexamethylphosphoric triamide, pyridine or benzyltriethylammonium chloride. The reaction temperature is preferably from 0 to 200° C., particularly preferably from 25° C. to 100° C. The reaction pressure is preferably from 0.1 to 10 MPa. The reaction time is preferably from 1 to 24 hours, particularly preferably from 1 to 6 hours.

The following compound (1) to be provided by the reaction of converting the compound (2) is a compound which has been produced and identified by the process of the present invention for the first time.

Among the production processes of the present invention, a process to obtain the compound (1) employing, as the compound (10) as a starting material, 1,3,5-trihydroxyadamantane or 1,3,5,7-tetrahydroxyadamantane as the starting material, is a very useful process in the process of the present invention employing the liquid phase fluorination method. This production process is a process which comprises subjecting the above compound (10A) to esterification reaction with the above compound (11) to obtain the above compound (12A), subjecting the compound (12A) to fluorination in a liquid phase to obtain the above compound (13A), subjecting the compound (13A) to hydrolysis or alcoholysis to obtain the above compound (2A), and reacting the compound (2A) with the compound (15) in such a proportion that at least three hydroxyl groups are reacted, to obtain a compound (1A).

In production of the compound (1A), in a case where the compound (2A) is in the trihydroxy-form, the compound (1)

wherein one to two hydroxyl groups remain, may be formed, and in a case where the compound (2) is in the tetrahydroxy-form, the compound (1) wherein one to three hydroxyl groups remain, may be formed. Such a compound wherein hydroxyl groups remain, is preferably a compound wherein all three Ys in the compound (1) are hydroxyl groups or a compound wherein two Ys are hydroxyl groups and one Y is a fluorine atom.

In a case where the compound (2) is in the dihydroxy-form, the compound (1) wherein one hydroxyl group remains may be formed by the reaction of the compound (2) with the compound (15). Such a compound (1) is preferably a compound wherein one $Y^0$ is a hydroxyl group and the other $Y^0$ is a fluorine atom. Such a compound wherein a hydroxyl group remains can be produce also by changing the amount of the compound (15) to be reacted with the compound (1) (or the compound (1A)).

In the process for producing the compound (1A), it is preferred that all of A, B, D, E, G and J are —$CF_2$—, or one of the specific hydrogen atoms in these groups is not fluorinated and all the remaining hydrogen atoms are fluorinated (that is, one group selected from A, B, D, E, G and J is —CFH—, and the other groups are —$CF_2$—).

$Y^0$ is a group corresponding to $Y^5$. Y corresponding to $Y^5$ which is a hydrogen atom is a hydrogen atom. Y corresponding to $Y^5$ which is a fluorine atom is a fluorine atom. $Y^5$ corresponding to $Y^5$ which is a hydroxyl group is a group represented by —OCOCR$^1$=CH$_2$ (wherein R$^1$ is as defined above) or a hydroxyl group.

$Y^0$ is preferably a group represented by the formula —OCO—CR$^1$=CH$_2$, a fluorine atom or a hydroxyl group, particularly preferably a group represented by the formula —OCO—CR$^1$=CH$_2$ or a fluorine atom. R$^1$ is preferably a hydrogen atom or a methyl group.

The compound (1) to be provided by the present invention is the following compound (1') wherein Y is as defined above. Definition of Y is substantially the same as $Y^0$. In this specification, groups represented by —OCO—CR$^1$=CH$_2$ and —OCO—CR$^{10}$=CH$_2$ will generically be referred to as a (meth)acryloyloxy group.

Examples of the compound (1) include the following compound (1C) having one (meth)acryloyloxy group, the following compound (1B) having two (meth)acryloyloxy groups and the following compound (1A') having three or four (meth)acryloyloxy groups:

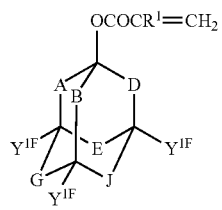
(1C)

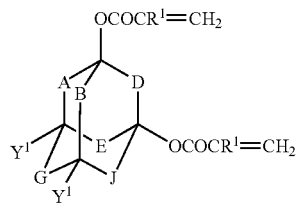
(1B)

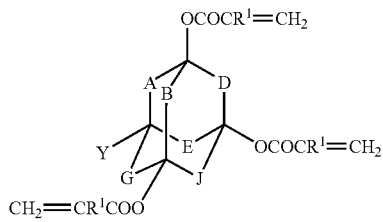
(1A')

In the above formulae, A, B, D, E, G, J and R$^1$ are as defined above.

In the compound (1C), $Y^{1F}$ is a fluorine atom or a hydroxyl group, and three $Y^{1F}$s may be the same or different. $Y^{1F}$ is preferably a fluorine atom.

In the compound (1B), $Y^1$ is a hydrogen atom, a fluorine atom or a hydroxyl group, and two $Y^1$s may be the same or different. $Y^1$ is preferably each independently a fluorine atom or a hydroxyl group. Further, it is preferred that two $Y^1$s are fluorine atoms, two $Y^1$s are hydroxyl groups, or one $Y^1$ is a fluorine atom and the other is a hydroxyl group. In the compound (1B), in a case where any of A to J is —CFH—, or in a case where $Y^1$ is a fluorine atom, D is preferably —CFH—.

In the compound (1A'), Y is a hydrogen atom, a fluorine atom, a hydroxyl group or a group represented by the formula —OCO—CR$^{10}$=CH$_2$ (wherein R$^{10}$ is a hydrogen atom, a methyl group, a fluorine atom or a trifluoromethyl group). Y is preferably a fluorine atom, a hydrogen atom or a (meth)acryloyloxy group.

Among the following compounds (1C) having one (meth)acryloyloxy group, a compound having the adamantane skeleton perfluorinated is represented by the formula (1CF), and among the compounds (1C), a compound wherein hydrogen remains, the following compound (1CH) may be mentioned. The symbols in the formulae are as defined above.

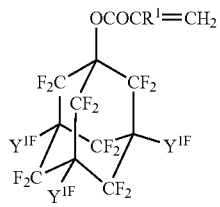
(1CF)

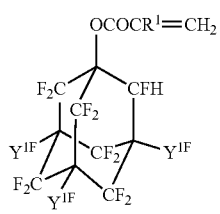
(1CH)

The following compounds may be mentioned as specific examples of the compound (1CF).

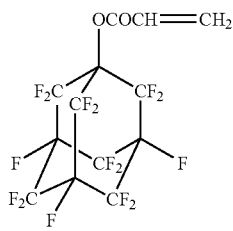
(1CF-1)

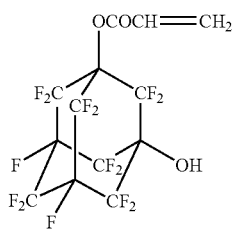
(1CF-2)

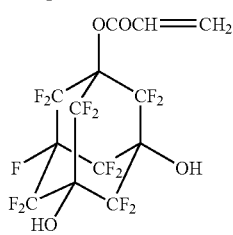

The following compounds may be mentioned as specific examples of the compound (1CH).

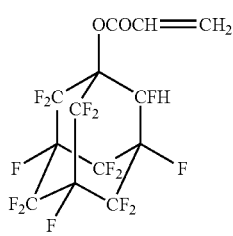
(1CH-1)

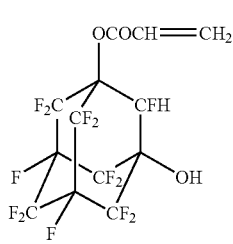
(1CH-2)

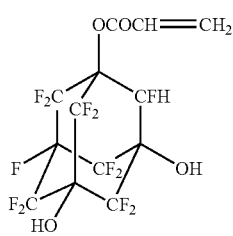

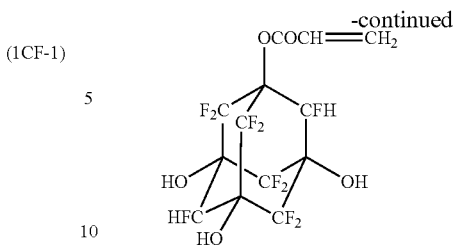

The compound (1CF-1) and the compound (1CH-1) wherein $Y^{1F}$ are fluorine atoms are novel compounds in that they show chemical shifts as disclosed in Examples under $^1$HNMR and $^{19}$FNMR measurement conditions disclosed in Examples of this specification.

Among the compounds (1B) having two (meth)acryloyloxy groups, a compound having the adamantane skeleton perfluorinated is represented by the formula (1BF), and among the compounds (1B), as the compound wherein hydrogen remains, the following compound (1BH) may be mentioned. The symbols in the formulae are as defined above.

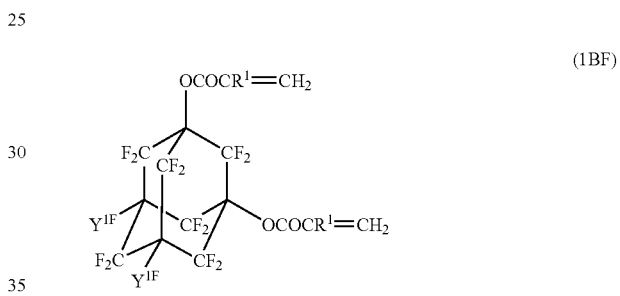
(1BF)

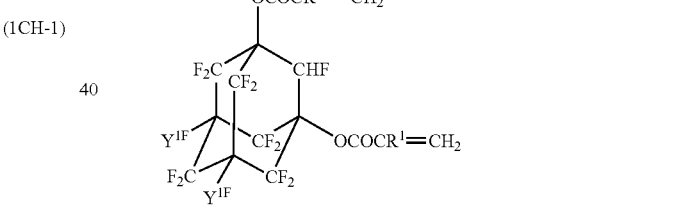
(1BH)

The following compounds may be mentioned as specific examples of the compound (1BF).

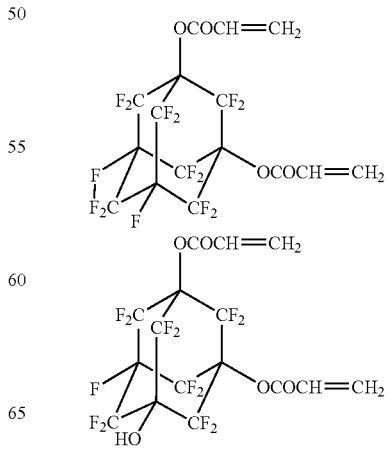

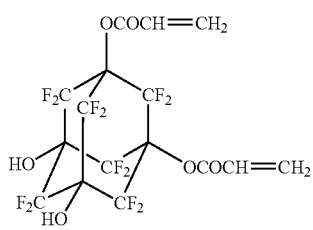

The following compounds may be mentioned as specific examples of the compound (1BH).

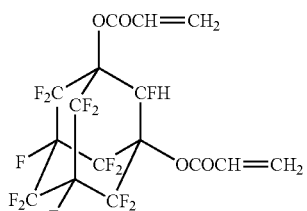

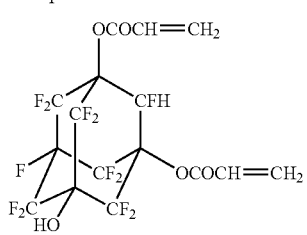

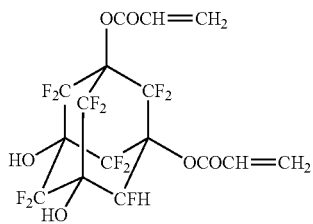

The compound (1B) is a novel compound in that its production process is provided by the production process of the present invention and it is identified for the first time.

The compound (1A') having three or four (meth)acryloyloxy groups is the same as the compound (1A) obtained by the above production process. Among the compounds (1A'), a compound having the adamantane skeleton perfluorinated is preferably the following compound (1AF), and among the compounds (1A'), as the compound wherein hydrogen remains, the following compound (1AH) is preferred.

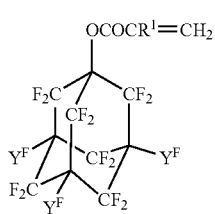
(1AF)

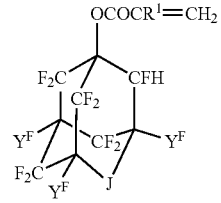
(1AH)

In the above, $R^1$ is as defined above, and $Y^F$s are such that two $Y^F$s are groups represented by the formula —OCO—$CR^{10}$=$CH_2$ and the other one $Y^F$ is a fluorine atom or a hydrogen atom ($Y^F$ is preferably a fluorine atom), or four $Y^F$s are groups represented by —OCO—$CR^{10}$=$CH_2$.

The following compounds may be mentioned as specific examples of the compound (1AF).

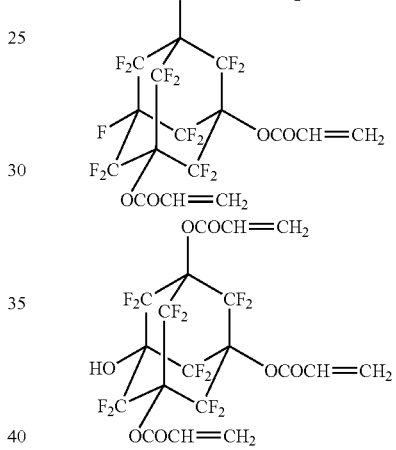

The following compounds may be mentioned as specific examples of the compound (1AH).

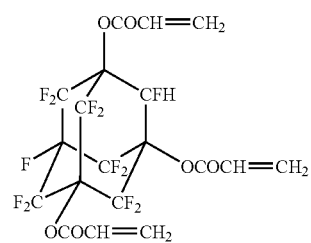

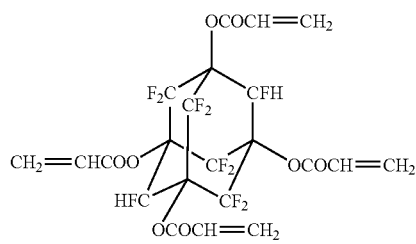

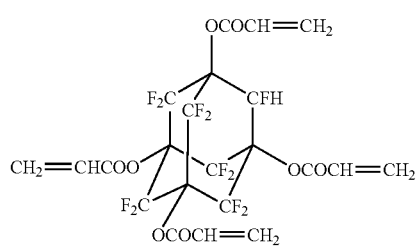

The present invention further provides the above compound (13) which is useful as an intermediate for production of the compound (1). In the following formulae, $R^F$ is as defined above, and its preferred embodiments are also as defined above.

The following compounds may be mentioned as specific examples of the compound (13) having the adamantane skeleton perfluorinated.

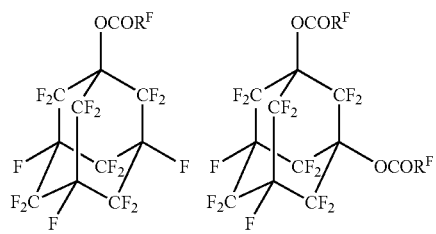

The following compounds may be mentioned as specific examples of the compound (13) in the case of the compound wherein hydrogen remains.

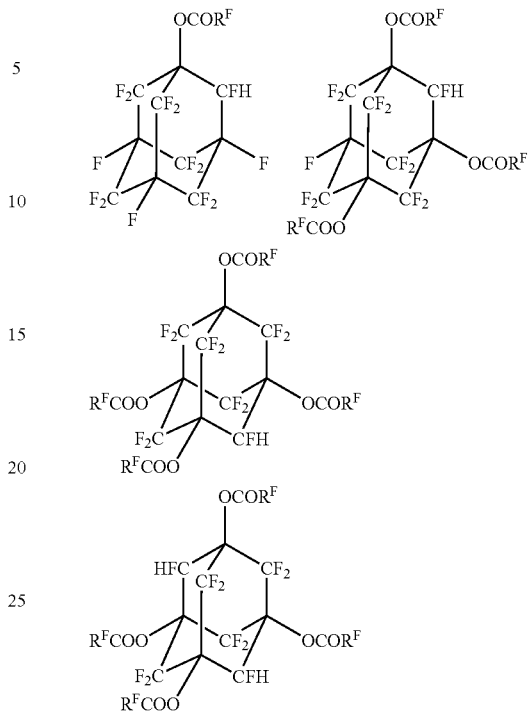

The following compounds may be mentioned as specific examples of the compound (2) having one hydroxyl group among the compounds (2) as an intermediate for production of the compound (1).

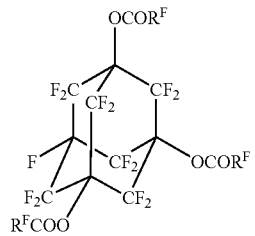
(2CF-1)

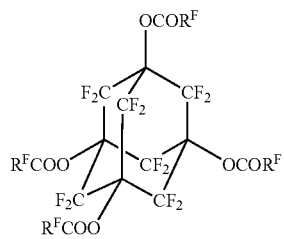
(2CH-1)

Among the compounds (2), compounds having two to four hydroxyl groups are novel compounds in that their production process is provided by the production process of the present invention and they are identified for the first time.

Among the compounds (2), as a compound having 3 or 4 hydroxyl groups, the following compound (2A') is preferred. In the following, $Y^{1F}$ is a fluorine atom or a hydroxyl group, and each of A to J is —CFH— or —CF$_2$—.

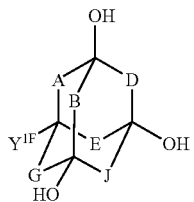
(2A')

Among the compounds (2A'), a compound having the adamantane skeleton perfluorinated is represented by the following formula (2AF), and the compound wherein hydrogen remains is represented by the following formula (2AH). The symbols in the following formulae are as defined above, and it is preferred that A, B, E, G and J are —$CF_2$— and D is —CFH—. A composition comprising the compound (2AF) and the compound (2AH) is also a novel composition.

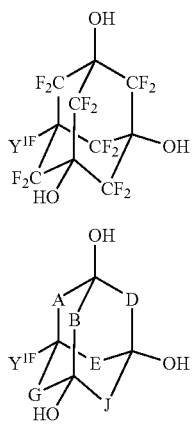
(2AF)

(2AH)

The following compounds may be mentioned as specific examples of the compound (2AF).

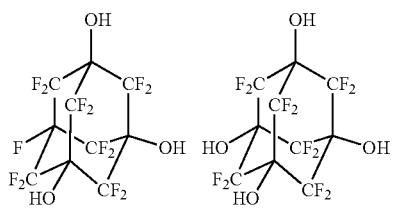

The following compounds may be mentioned as specific examples of the compound (2AH) wherein hydrogen remains.

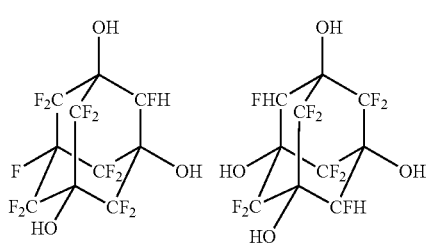

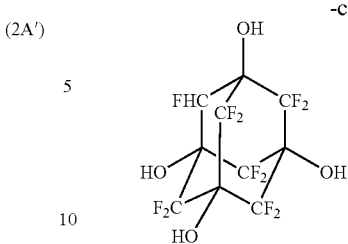
-continued

The following compound (2BF) may be mentioned as a compound having two hydroxyl groups among the compounds (2).

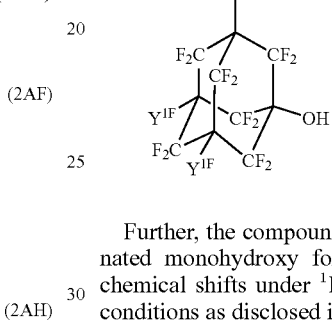
(2BF)

Further, the compound (2CF-1) which is in the perfluorinated monohydroxy form, is a compound which shows chemical shifts under $^1$HNMR and $^{19}$FNMR measurement conditions as disclosed in Examples of this specification.

The compound (1) provided by the present invention is a compound having a (meth)acryloyl group which is a polymerizable unsaturated group. A polymer to be obtained from this compound has a fluorinated adamantane structure in its side chains. Since the fluorinated adamantane structure is a very rigid structure, a hard polymer with a small volume change will be obtained. Further, a polymer having various functions derived from fluorine atoms will be provided.

Further, according to the present invention, a partially fluorinated compound (1) will be provided. The proportion of hydrogen atoms in the partially fluorinated compound (1) will easily be changed by adjusting the reaction conditions for the fluorination reaction. Further, by the presence of the specific hydrogen atom which is hardly fluorinated, it is also possible to produce the compound (1) wherein the atomic weight of such a hydrogen atom or the bonding position of the hydrogen atom is specified. A polymer obtained by polymerizing the compound (1) containing hydrogen atoms differs in the refractive index and the solubility in a solvent from a polymer obtained by polymerizing the perfluorinated compound (1). Accordingly, the content of hydrogen atoms should be adjusted depending upon desired physical properties.

The polymer obtained by polymerizing the compound (1) may be a polymer obtained by polymerizing only the compound (1) or a polymer obtained by polymerizing the compound (1) with another polymerizable compound copolymerizable with the compound (1) (hereinafter referred to as a comonomer). The type of the comonomer may be properly changed depending upon the purpose of use of the polymer.

The polymer provided by the present invention is a material applicable to fine photolithographic material, optical adhesives, etc. For example, as photolithographic material, a high level of etching resistance will be provided. The reason is considered to be such that in an adamantane skeleton having a structure wherein cyclic compounds are bonded to one another, even if part of bonds is broken by a laser beam, the compound hardly undergoes decomposition, and that C—F structures are less likely to undergo decomposition than C—H structures, and the carbon-carbon bonds are stronger.

EXAMPLES

Now, the present invention will be described in further detail with reference to Examples. However, it should be understood that the present invention is by no means restricted to such specific Examples.

In Examples, 1,1,2-trichloro-1,2,2-trifluoroethane will be referred to as R-113, and dichloropentafluoropropane as R-225. As R-225, a mixed product of $CF_3CF_2CHCl_2$ and $CF_2ClCF_2CHFCl$ was used. Gas chromatography will be referred to as GC, and the results in the GC analyses are shown by the peak area ratios. Gas chromatography mass spectrometry will be referred to as GC-MS. The pressure in Examples is shown by a gauge pressure.

Example 1

Example for Preparation of 1,3,5-trisacryloyloxy(fluoroadamantane)

Example 1-1

Esterification of 1,3,5-trihydroxyadamantane 1,3,5-trihydroxyadamantane (5.15 g) was dissolved in dimethylacetamide (55 mL) and charged into an autoclave, perfluoroisobutyloyl fluoride (86 g) was fed dividedly four times, followed by reaction at 25° C. for 64 hours. After purging with nitrogen gas, the reaction mixture was neutralized with a sodium bicarbonate water, followed by extraction with R-225, and the organic layer was concentrated and left to stand, and the precipitated crystals were subjected to filtration and recovered (14.9 g). The crystals (2.3 g) were recovered from the filtrate. The yield was 80%. The obtained crystals were put together and recrystallized from R-225/hexane (2/1 volume ratio) to obtain colorless crystals of 1,3,5-tris(perfluoroisobutyloxy)adamantane with a recovery rate of 50%.

$^1$H-NMR (300.4 MHz, solvent: $CDCl_3$, standard: TMS) δ (ppm): 2.21 (6H), 2.59 to 2.75 (7H).
$^{13}$C-NMR (100.53 MHz, solvent: $CDCl_3$, standard: TMS) δ (ppm): 28.9, 37.8, 43.0, 84.4, 86.7, 88.9, 118.7, 156.1).
$^{19}$F-NMR (282.7 MHz, solvent: $CDCl_3$, standard: $CFCl_3$) δ (ppm): −74.7 (18F), −180.7 (3F).
IR (KBr): 1,772, 1,785 cm$^{-1}$.

Example 1-2

Fluorination of 1,3,5-tris(perfluoroisobutyloyloxy)adamantane

R-113 (312 g) was charged into a 500 mL autoclave made of nickel, stirred and maintained at 25° C. At a gas outlet of the autoclave, a condenser maintained at 20° C., a NaF pellet packed layer and a condenser maintained at −10° C. were installed in series. Further, from the condenser maintained at −10° C., a liquid-returning line was installed to return the condensed liquid to the autoclave. After nitrogen gas was blown to the autoclave at 25° C. for one hour, fluorine gas diluted to 20% with nitrogen gas (hereinafter referred to as 20% diluted fluorine gas) was blown at 25° C. at a flow rate of 5.47 L/h for one hour. Then, while the 20% diluted fluorine gas was blown at the same flow rate, a solution having the crystals (5 g) of 1,3,5-tris(perfluoroisobutyloyloxy)adamantane obtained in Example 1-1 dissolved in R-113 (100 g) was injected over a period of 2.8 hours.

Then, while the 20% diluted fluorine gas was blown at the same flow rate and the pressure of the reactor was maintained at 0.15 MPa, a R-113 solution having a benzene concentration of 0.01 g/mL was injected in an amount of 9 mL while the temperature was raised from 25° C. to 40° C., whereupon the benzene solution inlet of the autoclave was closed, and stirring was continued for 0.3 hour.

Then, while the internal pressure of the reactor was maintained at 0.15 MPa and the internal temperature of the reactor was maintained at 40° C., 6 mL of the benzene solution mentioned above was injected, the benzene solution inlet of the autoclave was closed, and stirring was continued for 0.3 hour. The same operation was repeated three times. The total amount of benzene injected was 0.33 g, and the total amount of R-113 injected was 33 mL.

Further, stirring was continued for one hour while the 20% diluted fluorine gas was blown at the same flow rate. Then, the internal pressure of the reactor was adjusted to atmospheric pressure and nitrogen gas was blown for one hour. As a result of $^1$H-NMR and $^{19}$F-NMR analysis of the product, fluorinated product of 1,3,5-tris(perfluoroisobutyloyloxy)adamantane was formed as the main product. According to GC analysis, the selectivity of 1,3,5-tris(perfluoroisobutyloyloxy) perfluoroadamantane which was a completely fluorinated product was 4%, the selectivity of 2-hydro-1,3,5-tris(perfluorobutyloyloxy)perfluoroadamantane was 80%, and the selectivity of 1,3,5-tris(perfluoroisobutyloyloxy)fluoroadamantane having at least two hydrogen atoms was 15%. The NMR spectrum data of the product are shown below.

1,3,5-Tris(perfluoroisobutyloyloxy) perfluoroadamantane $^{19}$F-NMR (282.7 MHz, solvent: $CDCl_3$, standard: $CFCl_3$) δ (ppm): −74.7, −106.1 to −121.1, −178.7, −180.1, −217.8 to −221.7.

2-Hydro-1,3,5-tris(perfluoroisobutyloyloxy) perfluoroadamantane $^1$H-NMR (300.4 MHz, solvent: $CDCl_3$, standard: TMS) δ (ppm): 7.72 to 7.92. $^{19}$F-NMR (282.7 MHz, solvent: $CDCl_3$, standard: $CFCl_3$) δ (ppm): −74.7, −106.1 to −121.1, −178.7, −180.1, −218.3, −219.1, −219.7.

Example 1-3

Decomposition Reaction of Fluorinated 1,3,5-tris(isobutyloyloxy)adamantane

The product obtained in Example 1-2 was concentrated and added to an ethanol solution (70 mL) of sodium hydroxide (5 g), and the precipitated solid was dissolved in R-225, followed by reflux with heating for 5 hours. Stirring was carried out at 25° C. for 19 hours, followed by reflux with heating further for 7 hours. After the reaction solution was left to cool, it was concentrated to obtain an orange mixture of solid and liquid. The mixture was neutralized with 3M hydrochloric acid and washed with R-225, the aqueous layer was concentrated, water was completely removed, followed by extraction with ethanol, and the extract was concentrated to obtain a solid (0.8 g). The solid was analyzed and as a result, formation of perfluoro(1,3,5-trihydroxyadamantane) and 2-hydro-perfluoro(1,3,5-trihydroxyadamantane) was confirmed. NMR spectrum data of the products are shown below.

Perfluoro(1,3,5-trihydroxyadamantane)

$^{19}$F-NMR (282.7 MHz, solvent: CD$_3$OD, standard: CFCl$_3$) δ (ppm): −117.2 to −124.4 (m), −220.6 to −222.2 (m).

2-Hydro-perfluoro(1,3,5-trihydroxyadamantane)

$^1$H-NMR (300.4 MHz, solvent: CD$_3$OD, standard: CD$_3$OD) δ (ppm): 3.7. $^{19}$F-NMR (282.7 MHz, solvent: CD$_3$OD, standard: CFCl$_3$) δ (ppm): −117.2 to 124.4 (m), −220.5 (m), −221.5 (m), −223.4 (m).

Example 1-4

Acryloylation of fluoro(1,3,5-trihydroxyadamantane)

The product (0.42 g) obtained in Example 1-3 was stirred in diethyl ether (10 mL), and after cooling with ice water, triethylamine (0.42 g) and acryloyl chloride (0.33 g) were added. Then, stirring was carried out at is 25° C. overnight, the solid was subjected to filtration, and then the filtrate was concentrated, and the residue was isolated by column chromatography to obtain a product (0.06 g). The product was analyzed and as a result, formation of 1,3,5-trisacryloyloxy(perfluoroadamantane) was confirmed. Further, formation of 2-hydro-1,3,5-trisacryloyloxy(perfluoroadamantane) was confirmed. The NMR spectrum data of the products are shown below.

1,3,5-Trisacryloyloxy(perfluoroadamantane $^1$H-NMR (300.4 MHz, solvent: CDCl$_3$, standard: TMS) δ (ppm): 6.06 to 6.65 (m). $^{19}$F-NMR (282.7 MHz, solvent: CDCl$_3$, standard: CFCl$_3$) δ (ppm): −112.3 to −121.9 (m) −219.2 (m).

2-Hydro-1,3,5-trisacryloyloxy(perfluoroadamantane)

$^1$H-NMR (300.4 MHz, solvent: CDCl$_3$, standard: TMS) δ (ppm): 6.06 to 6.65 (m). $^{19}$F-NMR (282.7 MHz, solvent: CDCl$_3$, standard: CFCl$_3$) δ (ppm): −112.3 to −121.9 (m) −219.4 (m), −220.3 (m), −220.8 (m).

Example 2

Example for Preparation of 1,3,5,7-tetrakisacryloyloxy(fluoroadamantane)

The same reactions as in Examples 1-1 to 1-4 are carried out except that 1,3,5-trihydroxyadamantane used in Example 1-1 is changed to 1,3,5,7-tetrahydroxyadamantane, whereupon formation of 1,3,5,7-tetrakisacryloyloxy(perfluoroadamantane) is confirmed. Further, formation of 2-hydro-1,3,5,7-tetrakisacryloyloxy(perfluoroadamantane) is confirmed.

Example 3

Example for Preparation of 1-acryloyloxy(fluoroadamantane)

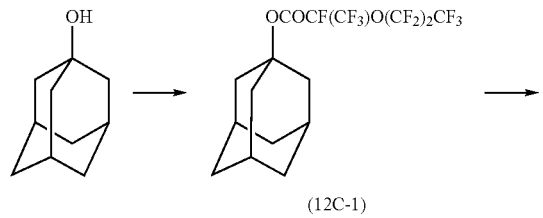

(12C-1)

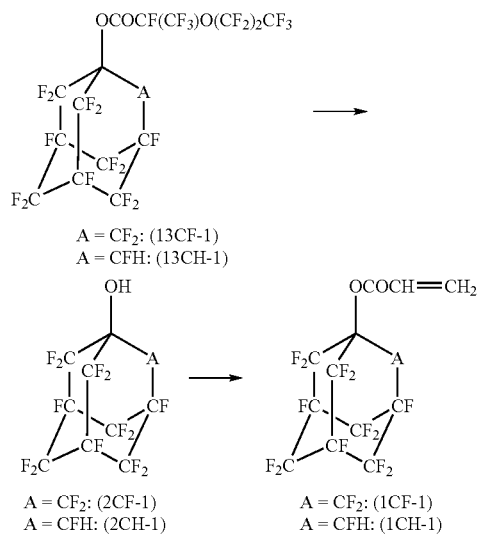

A = CF$_2$: (13CF-1)
A = CFH: (13CH-1)

A = CF$_2$: (2CF-1)
A = CFH: (2CH-1)

A = CF$_2$: (1CF-1)
A = CFH: (1CH-1)

Example 3-1

Example for Preparation of Compound (12C-1) by Esterification Reaction of 1-hydroxyadamantane 1-Adamantanol (3.09 g, 20.3 mmol) and sodium fluoride (0.95 g, 22.6 mmol) were put into a 50 mL round-bottomed flask, and CF$_3$(CF$_2$)$_2$OCF(CF$_3$)COF (9.94 g, 29.9 mmol) was dropwise added at 25° C. with stirring. After completion of the dropwise addition, stirring was carried out while the temperature was raised to 50° C., and stirring was continued for 9 hours while the internal temperature was maintained at from 45 to 50° C. R-225 was added for dilution, then sodium fluoride was removed by filter paper, followed by washing with water, whereupon magnesium sulfate was added, and the mixture was left to stand overnight. Magnesium sulfate was removed by filtration, and the filtrate was concentrated by an evaporator to obtain 8.80 g of a crude liquid. As a result of analyses by GC and NMR, it was confirmed that compound (12C-1) was formed at a selectivity of 99.8% and in a yield of 93.2%. The spectrum data of the compound (12C-1) are as follows.

$^1$H-NMR (300.4 MHz, solvent: CDCl$_3$, standard: TMS) δ (ppm): 1.69 (s, 6H), 2.15 (s, 6H), 2.24 (s, 3H).
$^{19}$F-NMR (282.7 MHz, solvent: CDCl$_3$, standard: CFCl$_3$) δ (ppm): −79.8 to −80.4 (1F), −81.7 (3F), −82.4 (3F), −86.4 to −87.0 (1F), −130.2 (2F), −131.7 (1F).

Example 3-2

Example for Preparation of Compound (13CF-1) and Compound (13CH-1) by Fluorination Reaction of 1-hydroxyadamantane Esterified at the 1-position The same autoclave as in Example 1-2 was prepared, and after blowing the 20% diluted fluorine gas at 25° C. at a flow rate of 13.22 L/hr for 30 minutes, the internal pressure of the autoclave was raised to 0.15 MPa, whereupon the same gas was blown further for 30 minutes. Then, while the 20% diluted fluorine gas was blown at the same flow rate, a solution having the compound (12C-1) (5 g) obtained in Example 2-1 dissolved in R-113 (100 g), was injected over a period of 4.2 hours.

A reaction was carried out under the same conditions as in Example 1-2 (provided that the benzene injection was carried out three times, and the total amount of benzene injected was 0.33 g, and the total amount of R-113 injected was 33 mL). After the reaction, the internal pressure of the reactor was adjusted to atmospheric pressure, and nitrogen gas was blown for one hour. The product was analyzed by $^{19}$F-NMR, whereby it was confirmed that compound (13CF-1) was contained in a yield of 83%. The product also contained compound (13CH-1).

$^{19}$F-NMR (282.7 MHz, solvent: CDCl$_3$, standard: CFCl$_3$) δ (ppm): −79.4 to −80.1 (1F), −81.7 to −82.2 (6F), −87.2 to −88.1 (1F), −113.5 to −124.5 (12F), −130.1 (2F), −131.2 (1F), −220.0 to −223.2 (3F).

Example 3-3

Example for Preparation of Compound (2CF-1) and Compound (2CH-1) by Hydrolysis

The fluorination product solution (8.4 g) obtained in Example 3-2 was charged into a 50 mL round-bottomed flask, and an ethanol solution containing 10 wt % of sodium hydroxide was dropwise added with stirring in a water bath. The temperature was slowly raised to 70° C. while stirring was continued, and after three hours, the stirring was stopped. A diluted HCl aqueous solution was slowly dropwise added until the liquid became acidic, and then t-butyl methyl ether was added thereto, followed by extraction twice. The obtained organic layer was concentrated by an evaporator and subsequently sufficiently evaporated to dryness by a vacuum pump to recover a pale yellow powder (7.3 g). As a result of analysis by GC, GC-MS and $^{19}$F-NMR, it was confirmed that compound (2CF-1), compound (2CH-1) and CF$_3$(CF$_2$)$_2$OCF(CF$_3$)COONa salt were contained in a ratio of compound (2CF-1):compound (2CH-1):CF$_3$(CF$_2$)$_2$OCF(CF$_3$)COONa salt=1.7:1.0:3.0 (molar ratio).

Compound (2CF-1): $^{19}$F-NMR (282.7 MHz, solvent: CDCl$_3$, standard: CFCl$_3$) δ (ppm): −121.5 (12F), −222.8 (3F).

Compound (2CH-1): $^1$H-NMR (300.4 MHz, solvent: CDCl$_3$, standard: TMS) δ (ppm): 5.24 (d, J$_{HF}$=48.1 Hz, 1H). $^{19}$F-NMR (282.7 MHz, solvent: CDCl$_3$, standard: CFCl$_3$) δ (ppm) −119.2 to 125.2 (10F), −213.5 (1F), −222.4 (1F), −223.5 (1F), −224.8 (1F).

Example 3-4

Example for Preparation of Compound (1CF-1) and Compound (1CH-1) by 1-acryloylation The powder (1.1 g) obtained in Example 3-3 was charged into a 50 mL round-bottomed flask, and diethyl ether (2.5 g) and triethylamine (0.2 g) were added thereto. This flask was put in an ice bath, and acrylic acid chloride (0.16 g) was slowly dropwise added thereto with stirring. Simultaneously with the dropwise addition, white precipitates were formed in the flask. After the entire acrylic acid chloride was dropwise added, the ice bath was removed, followed by stirring at 25° C. for 10 hours. This reaction solution was washed with deionized water to remove the formed white precipitates, and the organic layer was separated. As a result of analysis by GC, GC-MS and $^{19}$F-NMR, it was confirmed that compound (1CF-1), compound (1CH-1) and unreacted compound (2CF-1) were main components. As determined by GC analysis, the reactivity of the compound (1CF-1) was 56%, the reactivity of the compound (1CH-1) was 97% and the selectivity of both the compounds (1CF-1) and (1CH-1) was 93%. The NMR spectrum data of these compounds are shown below.

Compound (1CF-1): $^1$H-NMR (300.4 MHz, solvent: CDCl$_3$, standard: TMS) δ (ppm): 6.08 (dd, J$_{HF}$=1.5, 10.2 Hz, 1H), 6.25 (dd, J$_{HF}$=10.2, 16.5 Hz, 1H), 6.57 (dd, J$_{HF}$=1.5, 16.5 Hz, 1H). $^{19}$F-NMR (282.7 MHz, solvent: CDCl$_3$, standard: CFCl$_3$) δ (ppm): −114.7 (6F), −121.2 (6F), −221.6 (3F).

Compound (1CH-1): $^1$H-NMR (300.4 MHz, solvent: CDCl$_3$, standard: TMS) δ (ppm): 6.16 (dd, J$_{HF}$=1.5, 10.5 Hz, 1H), 6.24 (dd, J$_{HF}$=10.5, 16.2 Hz, 1H), 6.64 (dd, J$_{HF}$=1.5, 16.2 Hz, 1H), 6.77 (dq, J$_{HF}$=45.4, 6.3 Hz, 1H). $^{19}$F-NMR (282.7 MHz, solvent: CDCl$_3$, standard: CFCl$_3$) δ (ppm): −113.4 to −124.8 (10F), −212.5 (1F), −222.2 (2F), −222.9 (1F).

Example 4

Acryloylation of fluoro(1,3,5-trihdyroxyadamantane)

The product (0.26 g) obtained in Example 1-3 was stirred in diethyl ether (5 mL), followed by cooling with ice water, and triethylamine (0.34 g) and acryloyl chloride (0.089 g) were added. Then, stirring was carried out at 25° C. overnight, and the solid was removed by filtration, the filtrate was concentrated, and residual products were separated by column chromatography to obtain a product (0.06 g). As a result of analysis of the product, formation of 1-acryloyloxy-3,5-dihydroxy(perfluoroadamantane) and 1,3-diacryloyloxy-5-hydroxy(perfluoroadamantane) was confirmed. Further, formation of 2-hydro-1-acryloyloxy-3,5-dihydroxy (perfluoroadamantane) and 2-hydro-1,3-diacryloyloxy-5-hydroxy(perfluoroadamantane) was confirmed. NMR spectrum data of the products are shown below.

1-Acryloyloxy-3,5-dihydroxy(perfluoroadamantane)

$^1$H-NMR (300.4 MHz, solvent: CDCl$_3$, standard: TMS) δ (ppm): 6.08 (dm, J=10.5 Hz), 6.21 (dd, J=10.5, 16.9 Hz), 6.51 (dm, J=16.9 Hz). $^{19}$F-NMR (282.7 MHz, solvent: CDCl$_3$, standard: CFCl$_3$) δ (ppm): −115.3 to −122.5 (m), −221 to −222 (m).

2-Hydro-1-acryloyloxy-3,5-dihydroxy(perfluoroadamantane)

$^1$H-NMR (300.4 MHz, solvent: CDCl$_3$, standard: TMS) δ (ppm): 6.08 (dm, J=10.5 Hz), 6.21 (dd, J=10.5, 16.9 Hz), 6.34 (dm, J=48 Hz), 6.51 (dm, J=16.9 Hz). $^{19}$F-NMR (282.7 MHz, solvent: CDCl$_3$, standard: CFCl$_3$) δ (ppm): −112.7 to −125.7 (m), −221.7 (m), −222.5 (m).

1,3-Diacryloyloxy-5-hydroxy(perfluoroadamantane)

$^1$H-NMR (300.4 MHz, solvent: CDCl$_3$, standard: TMS) δ (ppm): 6.06 to 6.65 (m). $^{19}$F-NMR (282.7 MHz, solvent: CDCl$_3$, standard: CFCl$_3$) δ (ppm): −111.9 to −121.9 (m), −218.8 to −222.3 (m).

2-Hydro-1,3-diacryloyloxy-5-hydroxy(perfluoroadamantane)

$^1$H-NMR (300.4 MHz, solvent: CDCl$_3$, standard: TMS) δ (ppm): 6.06 to 6.65 (m). $^{19}$F-NMR (282.7 MHz, solvent:

CDCl$_3$, standard: CFCl$_3$) δ (ppm): −113.6 to −121.9 (m), −219.4 (m), −220.5 (m), −222.1 (m).

Example 5

Example for Preparation of 1,3-diacryloyloxy(fluoroadamantane)

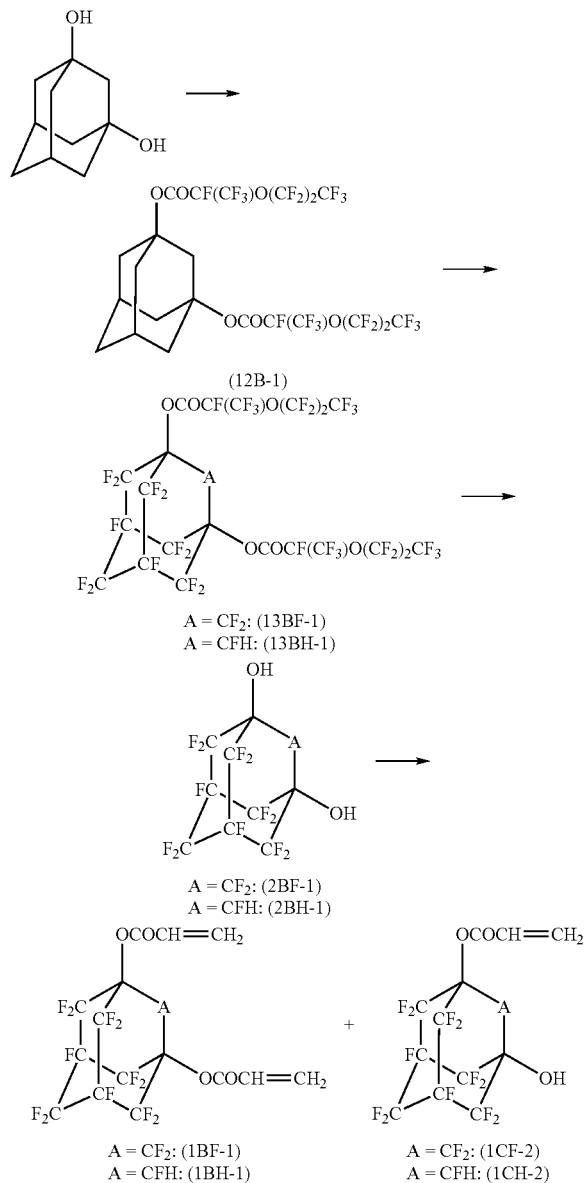

Example 5-1

Esterification Reaction of 1,3-dihydroxyadamantane 1,3-dihydroxyadamantane (2.01 g, 11.9 mmol) and 1.51 g (35.9 mmol) of sodium fluoride were put in a 50 mL round-bottomed flask, and R-225 was added, followed by stirring in a suspension state. CF$_3$(CF$_2$)$_2$OCF(CF$_3$)COF (11.23 g, 33.8 mmol) was dropwise added at room temperature while stirring was continued. After completion of the dropwise addition, stirring was carried out while the temperature was raised to 70° C., and stirring was continued for 12 hours while the internal temperature was maintained at from 60 to 65° C. R-225 was added for dilution, and sodium fluoride was removed by a filter paper, and the obtained solution was concentrated by an evaporator to remove R-225 and the excess CF$_3$(CF$_2$)$_2$OCF(CF$_3$)COF. This concentrated liquid was subjected to liquid-liquid separation twice with a sodium bicarbonate water and R-225, and the obtained organic layer was washed with water twice, magnesium sulfate was added thereto, and the organic layer was left at rest overnight. Magnesium sulfate was removed by filtration, and the organic layer was concentrated by an evaporator and a vacuum pump to obtain a colorless solution (8.28 g). As a result of analysis by GC and NMR, it was confirmed that compound (12B-1) was obtained with a selectivity of 95.4% and a yield of 83.4%.

$^1$H-NMR (300.4 MHz, solvent: CDCl$_3$, standard: TMS) δ (ppm): 1.65 (s, 2H), 2.09 to 2.26 (m, 8H), 2.51 (s, 4H).
$^{19}$F-NMR (282.7 MHz, solvent: CDCl$_3$, standard: CFCl$_3$) δ (ppm): −78.9 to −79.4 (2F), −81.1 (6F), −81.8 (6F), −86.0 to −86.5 (2F), −129.2 (4F), −130.9 (2F).

Example 5-2

Fluorination of Compound (12B-1)

Into a 500 mL autoclave made of nickel, R-113 (312 g) was introduced, stirred and maintained at 25° C. At a gas outlet of the autoclave, a condenser maintained at 20° C., a NaF pellet packed layer and a condenser maintained at −10° C. were installed in series. Further, from the condenser maintained at −10° C., a liquid returning line was installed to return the condensed liquid to the autoclave. After nitrogen gas was blown to the autoclave at room temperature for one hour, fluorine gas diluted to 20% with nitrogen gas (hereinafter referred to as 20% diluted fluorine gas) was blown at room temperature at a flow rate of 10.6 L/h for 30 minutes, and then the internal pressure of the autoclave was raised to 0.15 MPa, and the 20% diluted fluorine gas was blown further for 30 minutes. Then, while the internal pressure of the reactor was maintained at 0.15 MPa and the 20% diluted fluorine gas was blown at the same flow rate, a solution having the product (4.7 g) obtained in Example 5-1 dissolved in R-113 (94.3 g) was injected over a period of 2.6 hours.

Then, while the 20% diluted fluorine gas was blown at the same flow rate and the internal pressure of the autoclave was maintained at 0.15 MPa, a R-113 solution having a benzene concentration of 0.01 g/mL was injected in an amount of 9 mL while the temperature was raised from 25° C. to 40° C., whereupon the benzene solution inlet of the autoclave was closed, and stirring was continued for 0.3 hour.

Then, while the internal pressure of the reactor was maintained at 0.15 MPa and the internal temperature of the reactor was maintained at 40° C., the above benzene solution (6 mL) was injected, whereupon the benzene solution inlet of the autoclave was closed, and stirring was continued for 0.3 hour. The same operation was further repeated three times. The total amount of benzene injected was 0.34 g and the total amount of R-113 injected was 33 mL.

Further, stirring was continued for one hour while the 20% diluted fluorine gas was blown at the same flow rate. Then, the internal pressure of the reactor was adjusted to atmospheric pressure, and nitrogen gas was blown for one hour. The product was analyzed by GC-MS, $^1$H-NMR and $^{19}$F-NMR and as a result, it was confirmed to contain compound (13BF-1) with a yield of 55%. Further, compound (13BH-1) was contained with a yield of 27%. Other main components among components were compounds having at least two hydrogen atoms present in the adamantane skeleton.

$^{19}$F-NMR of compound (13BF-1) (282.7 MHz, solvent: CDCl$_3$, standard: CFCl$_3$) δ (ppm): −79.3 to −80.4 (2F), −81.8 to −82.4 (12F), −87.2 to −88.2 (2F), −109.2 to −121.4 (12F), −130.1 (4F), −129.7 to −131.9 (2F), −219.1 to −220.7 (2F).

$^1$H-NMR of compound (13BH-1) (300.4 MHz, solvent: CDCl$_3$, standard: TMS) δ (ppm): 7.81 (d, J$_{HF}$=430.6 Hz, 1H)

$^{19}$F-NMR of compound (13BH-1) (282.7 MHz, solvent: CDCl$_3$, standard: CFCl$_3$) δ (ppm): −79.3 to −80.4 (2F) −81.8 to −82.4 (12F), −87.2 to −88.2 (2F), −109.2 to −121.4 (10F), −130.1 (4F), −129.7 to −131.9 (2F), −218.5 to −221.3 (3F).

Example 5-3

Decomposition Reaction of Compound (2BF-1) and Compound (2BH-1)

The solution (11.8 g) of the products obtained in Example 5-2 was charged into a 100 mL round-bottomed flask, and a methanol solution (24 g) containing 15 wt % of sodium hydroxide was dropwise added thereto. The flask was heated while stirring was continued, followed by reflux for 11 hours, and then the flask was left to cool. A diluted HCl aqueous solution was slowly dropwise added until the liquid became neutral, and t-butyl methyl ether was added, followed by extraction three times. The obtained organic layer was concentrated by an evaporator and subsequently sufficiently evaporated to dryness by a vacuum pump to recover a pale yellow powder (3.8 g). As a result of analysis by $^{19}$F-NMR, the powder was confirmed to contain compound (2BF-1), compound (2BH-1) and CF$_3$(CF$_2$)$_2$OCF(CF$_3$)COONa salt.

$^{19}$F-NMR of compound (2BF-1) (282.7 MHz, solvent: CD$_3$OD, standard: CFCl$_3$) δ (ppm): −117.6 to −124.4, −221.5 to −224.5.

$^1$H-NMR of compound (2BH-1) (300.4 MHz, solvent: CDCl$_3$, standard: TMS) δ (ppm): 4.95 (dm, J$_{HF}$=47.8 Hz, 1H)

$^{19}$F-NMR of compound (2BH-1) (282.7 MHz, solvent: CD$_3$OD, standard: CFCl$_3$) δ (ppm): −118.1 to −123.9 (10F) −221.6 (1F), −222.5 (1F), −223.5 (dm, J=48 Hz, 1F).

Example 5-4

Acryloylation of Compound (2BF-1) and Compound (2BH-1)

The solid (3.9 g) obtained in Example 5-3 was charged into a 100 mL round-bottomed flask, and t-butyl methyl ether (30 mL) and triethylamine (2.03 g) were added thereto. This flask was put in an ice bath, and acrylic acid chloride (1.63 g) was slowly dropwise added thereto with stirring. Simultaneously with the dropwise addition, white precipitates were formed in the flask. After the entire acrylic acid chloride was dropwise added, the ice bath was removed, followed by stirring at 25° C. for 19 hours. Part of this reaction solution was concentrated and analyzed by NMR, whereby formation of compound (1BF-1), compound (1BH-1), compound (1CF-2) and compound (1CH-2) was confirmed. Further, unreacted compound (2CF-1) was also contained. As determined by GC analysis, the reactivity of the compound (1CF-2) was 56%, the reactivity of the compound (1CH-2) was 97%, and the selectivity of both the compounds (1CF-2) and (1CH-2) was 93%. NMR spectrum data of the reaction solution are shown below.

$^1$H-NMR (300.4 MHz, solvent: CDCl$_3$, standard: TMS) δ (ppm): 6.09 to 6.73 (m), 8.02 (dt, J=42, 6.6 Hz). $^{19}$F-NMR (282.7 MHz, solvent: CDCl$_3$, standard: CFCl$_3$) δ (ppm): −113.5 to −121.8 (m), −219.6 (m), −221.1 (m), −221.5 (m).

INDUSTRIAL APPLICABILITY

According to the production process of the present invention, adamantane derivatives which can be material compounds of a polymer excellent in etching resistance and having improved transmittance to light having a short wavelength, can be produced by an economically advantageous process from readily available materials.

A polymer produced by the process of the present invention may be suitably used e.g. as materials for microprocessing technology which are excellent in etching resistance and have improved transmittance to light having a short wavelength.

The entire disclosure of Japanese Patent Application No. 2004-178331 filed on Jun. 16, 2004 including specification, claims and summary is incorporated herein by reference in its entirety.

The invention claimed is:

1. A compound represented by the following formula (2A'):

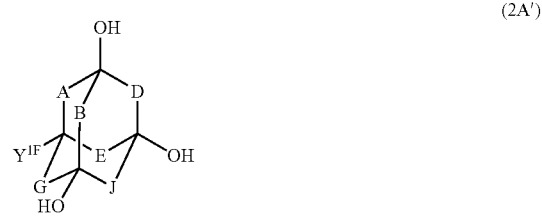

wherein

Y$^{1F}$ is a fluorine atom or a hydroxyl group;

A, B, D, E, G, J: each independently may be the same or different, is —CFH— or —CF$_2$—, and at least one of A, B, D, E, G and J is —CFH—.

2. The compound according to claim 1, wherein Y$^{1F}$ is a fluorine atom, and in $^{19}$FNMR (solvent CD$_3$OD, standard substance: CFCl$_3$) spectrum, the chemical shifts (unit: ppm) are −117.6 to −124.4 and −221.5 to −224.5.

* * * * *